(12) United States Patent
Dockrill et al.

(10) Patent No.: US 10,036,690 B2
(45) Date of Patent: Jul. 31, 2018

(54) BIOLOGICAL SAMPLE TREATMENT APPARATUS

(71) Applicant: LEICA BIOSYSTEMS MELBOURNE PTY LTD, Mount Waverly, Victoria (AU)

(72) Inventors: Mark Brian Dockrill, Chadstone (AU); Samuel Gason, Carnegie (AU)

(73) Assignee: LEICA BIOSYSTEMS MELBOURNE PTY LTD, Mt. Waverly, Victoria (AU)

( * ) Notice: Subject to any disclaimer, the term of this patent is extended or adjusted under 35 U.S.C. 154(b) by 1070 days.

(21) Appl. No.: 14/358,375

(22) PCT Filed: Nov. 15, 2012

(86) PCT No.: PCT/AU2012/001415
§ 371 (c)(1),
(2) Date: May 15, 2014

(87) PCT Pub. No.: WO2013/071358
PCT Pub. Date: May 23, 2013

(65) Prior Publication Data
US 2014/0342358 A1    Nov. 20, 2014

Related U.S. Application Data

(60) Provisional application No. 61/560,569, filed on Nov. 16, 2011.

(51) Int. Cl.
*C12M 3/00* (2006.01)
*G01N 1/31* (2006.01)
*G01N 35/00* (2006.01)

(52) U.S. Cl.
CPC .............. *G01N 1/31* (2013.01); *G01N 1/312* (2013.01); *G01N 35/00029* (2013.01); *G01N 2035/00079* (2013.01)

(58) Field of Classification Search
None
See application file for complete search history.

(56) References Cited

U.S. PATENT DOCUMENTS

| | | | | |
|---|---|---|---|---|
| 6,183,693 | B1 * | 2/2001 | Bogen | B01L 7/52 219/385 |
| 6,387,326 | B1 | 5/2002 | Edwards et al. | |
| 7,514,042 | B2 * | 4/2009 | Lihl | G01N 1/31 422/536 |
| 2002/0116132 | A1 * | 8/2002 | Rhett | G01N 1/312 702/19 |
| 2005/0186114 | A1 * | 8/2005 | Reinhardt | B01L 9/52 422/65 |
| 2006/0088940 | A1 * | 4/2006 | Feingold | G01N 1/30 436/47 |
| 2006/0148063 | A1 * | 7/2006 | Fauzzi | G01N 1/31 435/286.4 |
| 2006/0171857 | A1 | 8/2006 | Stead et al. | |
| 2006/0178776 | A1 * | 8/2006 | Feingold | G01N 35/0092 700/245 |
| 2009/0017491 | A1 | 1/2009 | Lemme et al. | |
| 2009/0098639 | A1 * | 4/2009 | Ljungmann | G01N 1/312 435/283.1 |
| 2009/0325309 | A1 * | 12/2009 | Favuzzi | G01N 35/1002 436/180 |
| 2010/0151513 | A1 * | 6/2010 | Vom | G01N 1/36 435/40.52 |
| 2011/0136135 | A1 * | 6/2011 | Larsen | G01N 1/2813 435/7.1 |
| 2013/0310964 | A1 * | 11/2013 | Yano | G01N 35/0092 700/112 |

FOREIGN PATENT DOCUMENTS

| | | |
|---|---|---|
| CN | 1726275 A | 1/2006 |
| CN | 1726386 A | 1/2006 |
| JP | 2006-220654 A | 8/2006 |
| JP | 2009-50968 A | 3/2009 |
| JP | 2011-524527 A | 9/2011 |
| WO | 02/13967 A2 | 2/2002 |
| WO | 2009/152569 A1 | 12/2009 |
| WO | 2010/078240 A1 | 7/2010 |
| WO | 2011/060387 A1 | 5/2011 |
| WO | 2011/069507 A1 | 6/2011 |

OTHER PUBLICATIONS

Communication dated Feb. 17, 2015, from the Australian Patent Office in counterpart Australian application No. 2012339621.
Communication dated Dec. 17, 2015 from the Australian Patent Office in counterpart Australian application No. 2012339621.
Communication dated Jan. 30, 2015, from the European Patent Office in counterpart European application No. 12849498.6.
Communication dated Nov. 4, 2015 from the State Intellectual Property Office of the P.R.C. in counterpart Chinese application No. 201280067151.8.
Communication dated Sep. 1, 2016 from the State Intellectual Property of the P.R.C. in counterpart Chinese application No. 201280067151.8.
Communication dated Oct. 4, 2016, from the Japanese Patent Office in counterpart Japanese application No. 2014-541484.
International Search Report of PCT/AU2012/001415 dated Jun. 5, 2013.
Chinese Office Action; dated May 3, 2017; Application No. 2012800671518 with English translation.
Japanese Office Action; Application No. 2014-541484; Leica Biosystems Melbourne PTY Ltd.; dated Oct. 3, 2017, with Partial English Translation.

* cited by examiner

*Primary Examiner* — Ann Y Lam
(74) *Attorney, Agent, or Firm* — Sughrue Mion, PLLC

(57) ABSTRACT

Apparatus for treating biological samples disposed on substrates, including: an input buffer for receiving one or more substrate holders each being adapted to support a plurality of the substrates; a treatment zone including a plurality of treatment stations each being adapted to receive one of the substrates; a reagent dispenser configured by a controller to dispense reagents to the substrates at the treatment stations; a substrate transport device configured by the controller to transport individual substrates between the substrate holders in the input buffer and the treatment stations.

19 Claims, 10 Drawing Sheets

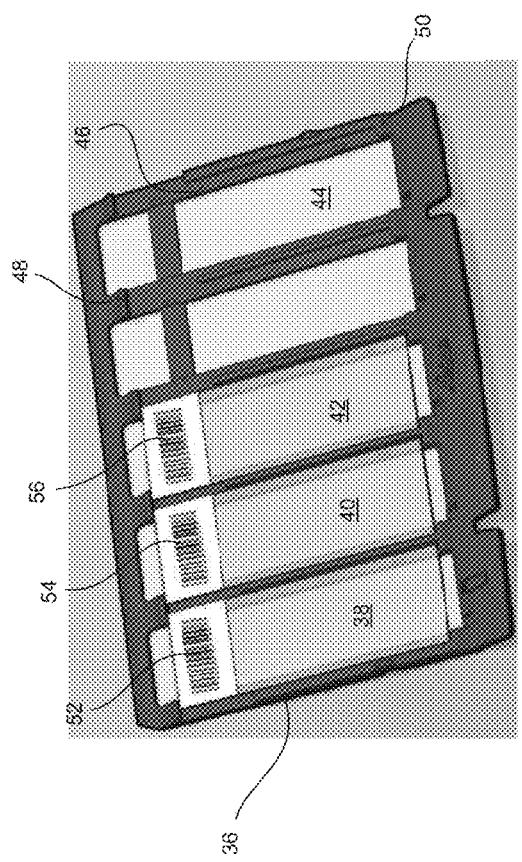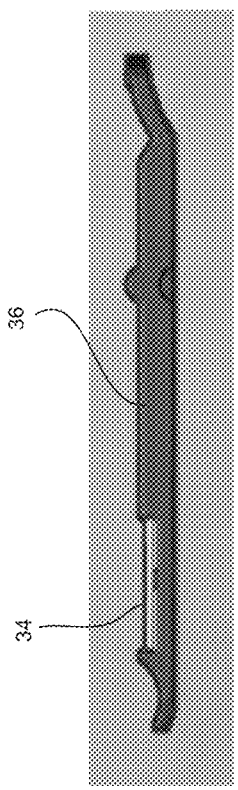
FIG. 4
FIG. 5

BIOLOGICAL SAMPLE TREATMENT APPARATUS

CROSS REFERENCE TO RELATED APPLICATIONS

This application is a National Stage of International Application No. PCT/AU2012/001415 filed Nov. 15, 2012, claiming priority based on U.S. Provisional Patent Application No. 61/560,569, filed Nov. 16, 2011, the contents of all of which are incorporated herein by reference in their entirety.

FIELD OF THE INVENTION

The present invention relates to an automated system and method of treating one or more biological samples disposed on substrates. The present invention is of particular, but not exclusive, application in treating tissue samples disposed on slides using a plurality of reagents to stain the tissue samples.

BACKGROUND OF THE INVENTION

There are many applications where it is desirable to initiate a chemical reaction on a sample. Commonly the samples are located on a microscope slide. Typical reactions include immuno-histochemical reactions of cellular material, or in situ-hybridisation of DNA or RNA. In other forms, microarrays of thousands of small samples of material, including DNA, RNA proteins or small chemical compounds are attached to a microscope slide, where it is desirable to promote a chemical reaction between the material on the slide and other chemicals or fluids. These reactions require controlled conditions, including controlled reaction time, temperature and concentration of chemicals.

In the past, chemical reactions taking place on slides were controlled by skilled persons adding and mixing the reagents. This allowed the time and quantity of the reagents to be controlled for each slide. However, this procedure was time consuming, required highly skilled operators, and could produce inconsistent results from slide to slide.

Attempts have been made to automatically treat tissue samples disposed on slides for immunologic applications using, for example, an automated tissue sample staining apparatus. In this example, the automated staining apparatus treats tissue samples using reagents to treat the sample before staining the samples on the slides. The treatment of the samples is typically performed automatically by one or more robots configured to dispense reagents to the samples on the slides in a predetermined sequence according to a staining protocol. In addition, the robots can also be configured to dispense reagents such as dewaxing solution and alcohol to treat the samples on slides before and after staining. The reagent currently being dispensed by one of the robots, however, must be purged from the robots before other reagents can be dispensed causing delay, reagent wastage and inefficient use of the automated staining apparatus.

In spite of these advances, existing tissue sample treatment methods comprise a number of steps that are performed manually. For example, in immunologic applications, such as in-situ hybridization (ISH) and immunohistochemical (IHC) applications, some steps including dewaxing and target retrieval are performed manually by an operator to treat the tissue sample before it can be used in a staining apparatus for staining the tissue sample according to a predetermined staining protocol.

It would be desirable to provide an apparatus for treating biological samples disposed on substrates which minimises the manual labour required to treat the samples. Moreover, there exists a need to provide such an apparatus which treats biological samples in a simple, time-efficient manner. There also exists a need to provide an apparatus for treating biological samples disposed on substrates which ameliorates and/or overcomes disadvantages or inconveniences of known automatically sample treatment apparatuses.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY

One aspect of the invention provides an apparatus for treating biological samples disposed on substrates. The apparatus includes an input buffer for receiving one or more substrate holders each being adapted to support a plurality of the substrates; a treatment zone including a plurality of treatment stations each being adapted to receive one of the substrates; a reagent dispenser configured by a controller to dispense reagents to the substrates at the treatment stations; and a substrate transport device configured by the controller to transport individual substrates between the substrate holders in the input buffer and the treatment stations.

In one or more embodiments, the apparatus further includes a substrate identification reader for reading, when the substrate is in the input buffer, a substrate identifier borne by each substrate; and a database for storing a plurality of protocols, each protocol defining a sequence of treatment operations to be applied to one or more substrates. In this case, the controller is further configured to cause the substrate transport device to group individual substrates within the treatment zone to efficiently treat the biological samples disposed on substrates.

The controller may be configured to cause the substrate transport device to group individual substrates to which a common protocol is to be applied.

The controller may be configured to cause the substrate transport device to group individual substrates to which a common reagent, such as an antibody, is to be applied.

The controller may be configured to cause the substrate transport device to group individual substrates which share a common treatment time, such as an epitope retrieval time.

The controller may be configured to cause the substrate transport device to transport the individual substrates so as to optimise throughput of the substrates during protocols and/or treatment operations in the apparatus.

The controller may be configured to optimise throughput by maximising the number of protocols or treatment operations that can be consecutively performed on one or more substrates.

Alternatively or additionally, the controller may be configured to optimise throughput by maximising the number of reagent dispensing operations performed by the reagent dispenser to different substrates without changing reagents.

In one or more embodiments, the substrate identification reader is supported by the substrate transport device.

In one or more embodiments, the reagent dispenser is supported by the substrate transport device.

In one or more embodiments, the apparatus further includes a substrate covering unit for applying a cover to the biological sample on the substrate. In this case, the substrate transport device is further adapted to transporting individual slides into and out of the substrate covering unit.

In one or more embodiments, the treatment stations are disposed on a work surface, and the apparatus further includes a plurality of reagent containers housed below the work surface; and a reagent transfer system for transferring reagent from the reagent containers to the reagent dispenser.

In one or more embodiments, the reagent transfer system includes a reagent transfer port passing through the work surface; and an aspiration probe for aspirating reagent from the reagent containers via the reagent transfer port.

In one or more embodiments, the reagent transfer system further includes a carousel supporting the reagent containers, the carousel being adapted to selectively bring each reagent container into fluidic communication with the reagent transfer port.

In one or more embodiments, the apparatus further includes a reagent container access port for loading and unloading the reagent containers from the carousel.

In one or more embodiments, the input buffer includes a plurality of input compartments each adapted to receive one or more of the substrate holders in a disposition whereby the substrates in the substrate holders are accessible to the substrate transport device.

One or more of the input compartments may include one or more baking stations for baking the substrates in the substrate holders.

In one or more embodiments, the apparatus further includes an output buffer for receiving one or more of the substrate holders, wherein the substrate transport device further configured by the controller to transport individual substrates between the treatment stations and the substrate holders in the output buffer.

In one or more embodiments, the output buffer includes a plurality of output compartments each adapted to receive one or more of the substrate holders in a disposition whereby the substrates in the substrate holders are accessible to the substrate transport device.

One or more of the output compartments may include one or more curing stations for curing the substrates in the substrate holders.

In one or more embodiments in which the input and/or output buffers include a plurality of compartments, those compartments are adapted to support the substrate holders in a substantially horizontal orientation.

At least one of the substrate holders received in the input buffer may support substrates from a common patient case, and the controller may be further configured to group substrates into at least one of the substrate holders received in the output buffer according to that common patient case. Grouping of substrates may be according to any desired configuration including, but not limited to, common patient case, marker batch, staining batch, specialized protocol, referring doctor, destined pathologist, or other preferred management configuration. In one or more embodiments, grouping of substrates may be configurable by the user according to desired groupings and/or preferences.

Another aspect of the invention provides an automated method for treating biological samples disposed on substrates, where the substrates are treated at treatment stations in a treatment zone. The method includes the steps of receiving one or more substrate holders in an input buffer, each substrate holder being adapted to support a plurality of the substrates; using a substrate transport device, configured by a controller, to transport individual substrates between the substrate holders in the input buffer and the treatment stations; and using one or more reagent dispensers, configured by the controller, to dispense reagents to the substrates at the treatment stations.

The method may further include the step of using the substrate transport device, configured by the controller, to transport individual substrates between the treatment stations and substrate holders in an output buffer for receiving one or more of the substrate holders.

The method may further include the step of using the substrate transport device, configured by the controller, to transport individual substrates into and out of a substrate covering unit for applying a cover member to the biological sample on the substrate.

Yet another aspect of the invention provides computer program code which when executed implements the above-described method.

A further aspect of the invention provides a tangible computer readable medium comprising the above-described program code.

A still further aspect of the invention provides a data file comprising the above-described program code.

BRIEF DESCRIPTION OF THE DRAWINGS

Embodiments of the present invention will now be described, by way of example only, with reference to the accompanying drawings, in which:

FIGS. 4 and 5 are respectively plan and side elevation views of a substrate holder, supporting substrates therein, for use with the apparatus of FIG. 1;

DETAILED DESCRIPTION OF THE DRAWINGS

Figure 1:
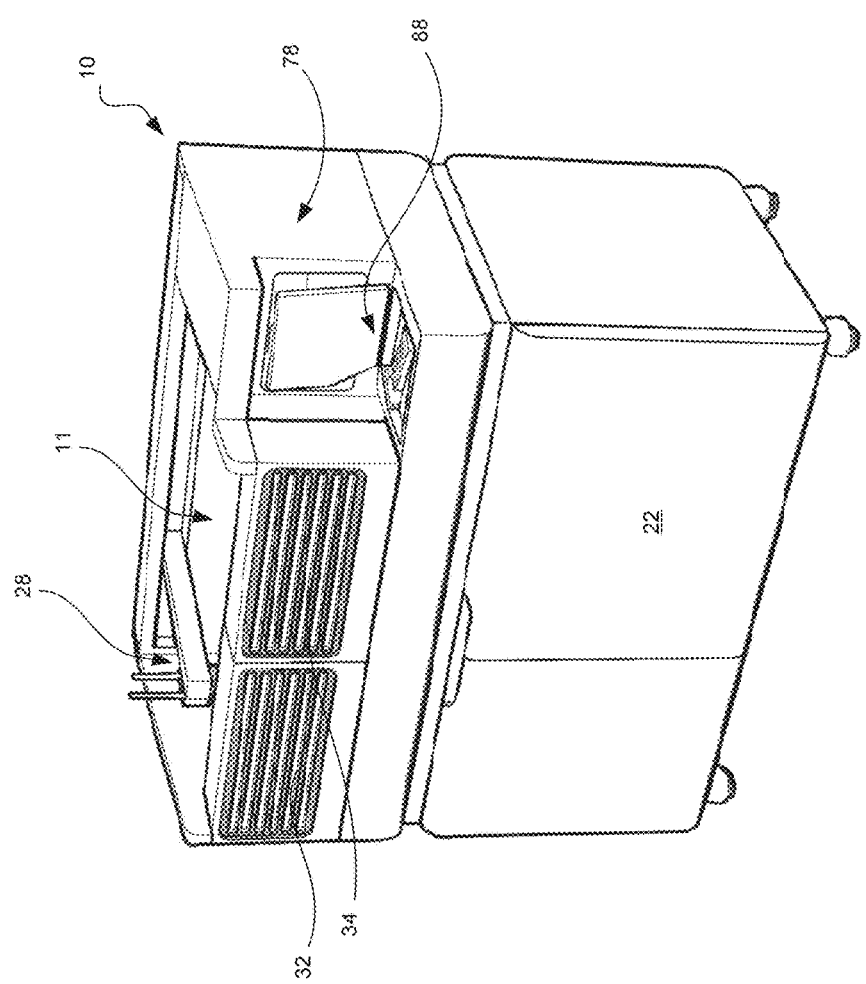
FIG. 1 is a perspective view of one embodiment of an apparatus for treating biological samples disposed on substrates.
Figure 2:
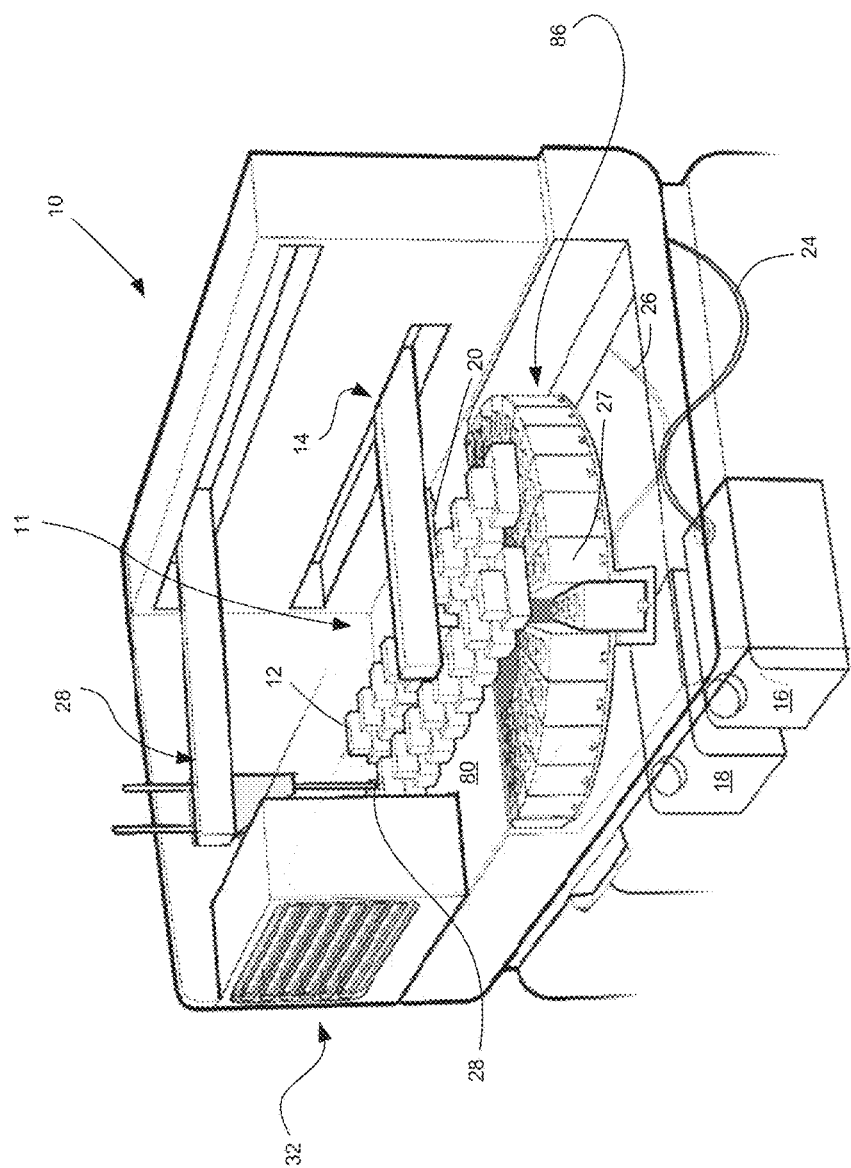
FIG. 2 is a section perspective view of the apparatus of FIG. 1.
Figure 3:
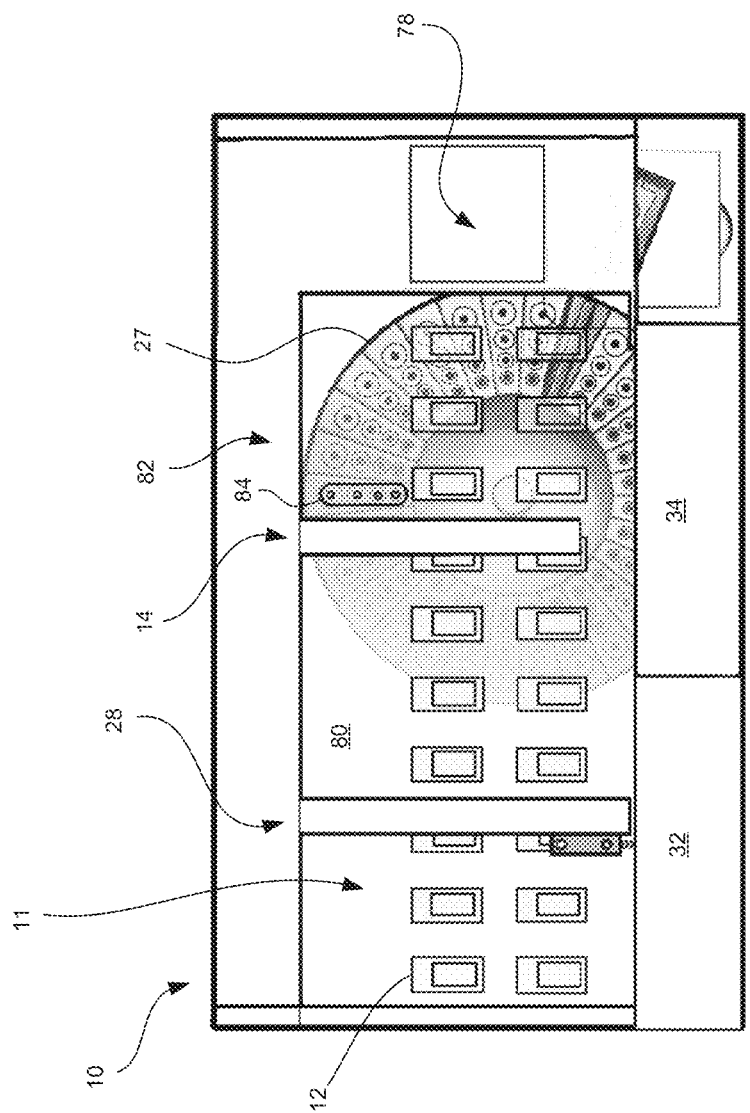
FIG. 3 is a plan view of the apparatus of FIG. 1.

Referring to FIGS. 1 to 3, there is shown generally an exemplary embodiment of an apparatus 10 for treating biological samples disposed on substrates, such as slides. The apparatus 10 includes a treatment zone 11 including a plurality of treatment stations, such as the treatment station referenced 12, each being adapted to receive one of the substrates.

The apparatus 10 also includes a Bulk Fluid Robot (BFR) 14 configured by a controller 60 (seen in FIG. 6), disposed within the apparatus 10, to dispense a plurality of reagents stored in reagent containers, such as those referenced 16 and 18, to the substrates at the treatment stations 12. The reagents are dispensed from the BFR 14 via an output nozzle 20 to treat the biological samples on the substrates. For example, the BFR 14 may be configured by the controller 60 to dispense reagents to the substrates such a oxalic acid, sulphuric acid, potassium permanganate, alcohol, dewaxing agent, haematoxylin, peroxide, EDTA, citric acid, DI water, and Bond™ wash, to treat the biological samples disposed on the substrates. The reagents (e.g. bulk fluid re-agents) stored in the reagent containers 16 and 18 are accessible via a panel 22 on the front of the apparatus 10.

The apparatus 10 also includes one or more pumps (not shown in this figure) and tubes, such as those referenced 24 and 26, for conveying reagents from the re-agent containers 16 and 18 to the output nozzle 20 of the BFR 14.

The apparatus 10 further includes a Fluid Transfer Probe (FTP) robot 28 configured by the controller 60 to dispense a plurality of high value reagents stored in high value reagent containers, such as the container referenced 27, to the substrates received by the substrate treatment stations 12 via an FTP output nozzle 30 disposed on the FTP robot 28. In use, the BFR 14 and the FTP robot 28 are configured by the controller 60 to dispense bulk fluid reagents and high value reagents in a predetermined sequence to treat the biological samples. In one example, the bulk fluid reagents and high value reagents are dispensed so as to stain the biological samples according to a predetermined staining protocol for in-situ hybridisation (ISH) and immunohistochemical (IHC) applications.

In one or more embodiments, liquid level sensing for reagents dispensed by the FTP robot may be desirable. Liquid level sensing may be performed using probe touch technology and/or by monitoring changes in capacitance or pressure at a dispensing output nozzle. Alternatively, optical liquid level sensing systems and/or ultrasonic systems may be employed. Measurements of reagent volumes taken at the inlet, in the chamber and/or through the outlet, can be compared by the controller 60 to cross check against the total volume of dispenses calculated according to the number of protocols performed. This cross check can then be used for inventory control of reagents stored on board the apparatus 10.

Suitable liquid level sensing devices and components may be incorporated into the apparatus 10—in communication with the reagent containers and the controller 60—to ensure continued operations by provision of adequate levels of reagents. The controller 60 may be configured to notify a user of impending reagent changeover, or facilitate management of reagent use and life span.

Moreover, reagent containers may comprise a variety of sizes, shapes and/or configurations necessary to facilitate adequate supply of reagent for a single reaction or multiple reactions without requiring container replacement and adequately reside within the architecture of the apparatus 10.

In one or more embodiments, a pre-loaded reagent system including multiple reagent containers and a support, such as a carousel or tray, for those containers may be loaded into the apparatus 10.

The apparatus 10 further includes an input buffer 32 for receiving one or more substrate holders each being adapted to support a plurality of the substrates prior to the treatment of the biological samples on those substrates at the treatment stations 12. In addition, the apparatus 10 includes an output buffer 34 for receiving one or more of the substrate holders, into which substrates are placed after treatment at the treatment stations 12. For the sake of clarification, in some embodiments, the input buffer may also function as the output buffer for example, a substrate removed from the input buffer for treatment may be returned to the same location, and hence buffer, after treatment.

FIGS. 4 and 5 depict an exemplary embodiment of a substrate holder 36 adapted to support a plurality of substrates. In this example, the substrate holder 36 is adapted to support a maximum of five substrates, although only the three slides 38, 40 and 42 are depicted in FIG. 4. In one or more embodiments, the substrate holder may be adapted to support from one to five substrates. In other embodiments, the substrate holder may be adapted to support from five to twenty substrates. In yet other embodiments, the substrate holder may be adapted to support from twenty to fifty substrates. Each substrate in the substrate holder 36 is maintained in position above an aperture, such as the aperture referenced 44, by a ledge 46 supporting at least part of the periphery of the substrate and shoulders, such as the shoulders referenced 48 and 50.

Each of the substrates 38 to 42 bears a machine readable substrate identifier, such as barcodes 52 to 56, to enable automated detection of the substrate identifier and hence identification of individual substrates in the substrate holder 36. Whilst barcodes have been used in this exemplary embodiment of the invention, it will be appreciated that RFID tags or any other machine readable devices may be used in alternative embodiments. Machine readable substrate identifier(s) may be located at any site such as reagent containers, substrate, slide mountant, coverslip magazine, cover member or any other such location to facilitate identification, inventory control or otherwise manage or control components or processes of the apparatus.

Figure 6:
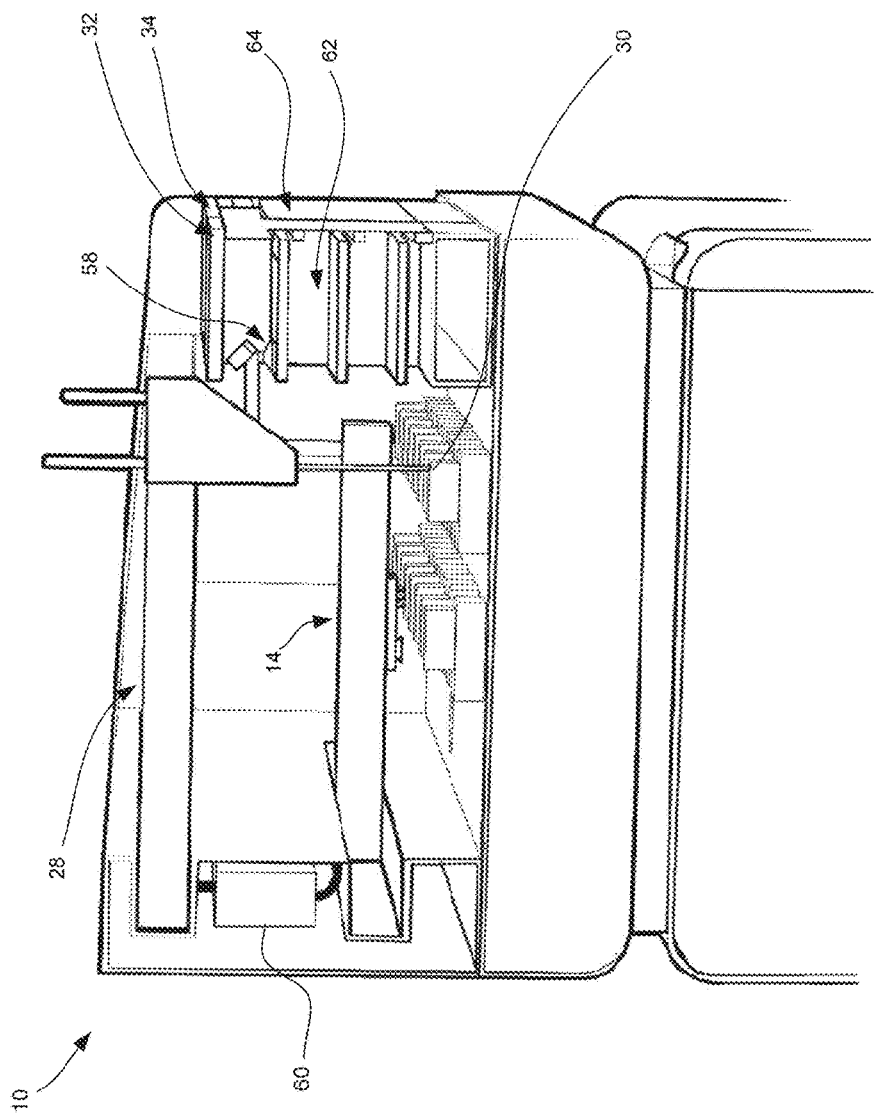
FIG. 6 is a side elevation view of vertical section taken through the apparatus of FIG. 1.

As best seen in FIG. 6, the input buffer 32 and output buffer 34 include a plurality of input compartments each adapted to receive one or more of the substrate holders in a disposition whereby the substrates in the substrate holders are accessible to a substrate transport device 58 configured by the controller 60 to transport individual substrates between the substrate holders in the input buffer, the treatment stations and the output buffer. For the sake of clarity, only two of the compartments, namely input compartment 62 and output compartment 64 are referenced in FIG. 6. The compartments in the input and output buffers are adapted to receive the substrate holders 36 in a substantially horizontal orientation.

In the apparatus 10, baking (at start of substrate treatment) and curing of covered substrates (at end of substrate treatment) can be completed at the input and output buffers respectively or at an intermittent station, or dedicated zone. In that regard, one or more of the input compartments of the input buffer 32 may include one or more baking stations (not shown) for baking the substrates in the substrate holders. Similarly, one or more of the output compartments of the output buffer 34 may include one or more curing stations for curing the substrates in the substrate holders. Operation of the baking/curing stations is controlled by the controller 60.

Figure 7:
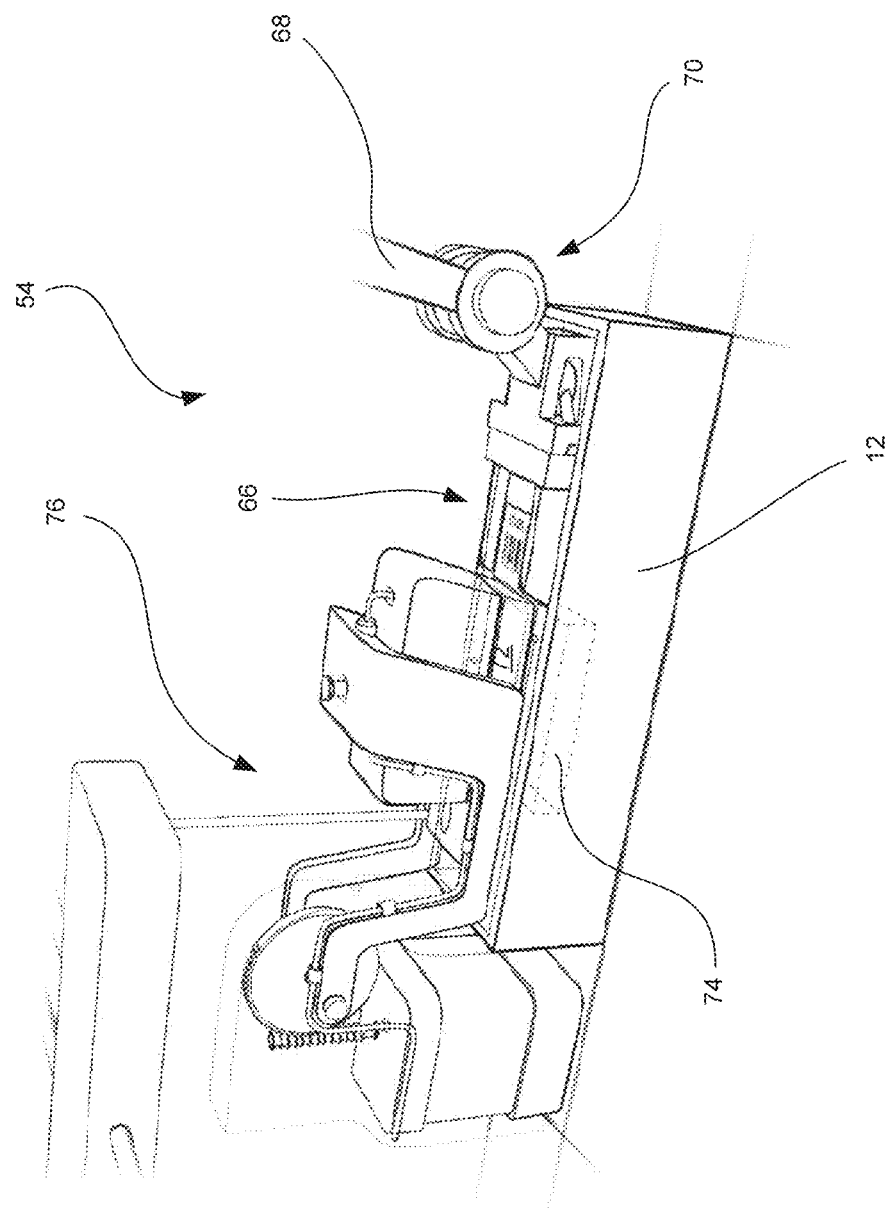
FIG. 7 is a perspective view of a treatment station, substrate transport device and cover tile placement device forming part of the apparatus of FIG. 1.

In this embodiment, the substrate transport device 58 forms part of the FTP robot 28. The FTP robot 28 is configured by the controller 60 to move the individual substrates in the apparatus 10 to the various treatment stations 12 for treatment of the biological samples disposed on the substrates. Accordingly, and as can be seen in more detail in FIG. 7, the substrate transport device 58 includes grippers 66, a robotic arm 68 and a pivot mechanism 70 operatively interconnecting the grippers and the arm.

The FTP robot 28 is configured by the controller 60 to displace the grippers in the X, Y and Z axes in order for each substrate to be individually gripped and moved from a substrate tray 36 (in an input compartment of the input buffer 32) to a first treatment station, and from the first treatment station to the second treatment station, and so on, in order that the biological sample can be treated according to a particular protocol. The FTP robot 28 is configured to then releasably hold and move each substrate to a selected substrate tray in a compartment of the output buffer 32, so that an operator can then subsequently remove the substrate tray from the apparatus 10.

The BFR 14 is configured by the controller 60 to move in the X, Y and Z axes in such a manner as to avoid interference with movement of the substrates by the FTP robot 28.

Each of the treatment stations 12 included in the apparatus 10 include a substrate support surface 72 upon which the substrate transport device 58 places an individual substrate during treatment operations. Disposed under the substrate support surface 72 is a thermal exchanger (heating pad) 74 operated by the controller 60 in order that baking, dewaxing or curing operations can be performed at each substrate treatment station 12. In addition, a cover member placement device 76 is provided to apply a cover member over the substrate prior to the application of reagent to the biological sample disposed on the substrate.

In a preferred embodiment, the cover member (not shown) is configured for use in an automated sample processing instrument. U.S. provisional patent applications 61/560,543 entitled "Cover Member, Method and Treatment Module for treating a Biological Sample on a Substrate" and 61/560,599 entitled "An Automated System and Method of Treating Tissue Samples on Slides" both filed by the same Applicant describe such instruments and the contents of those applications are hereby incorporated herein by reference.

Figure 8:
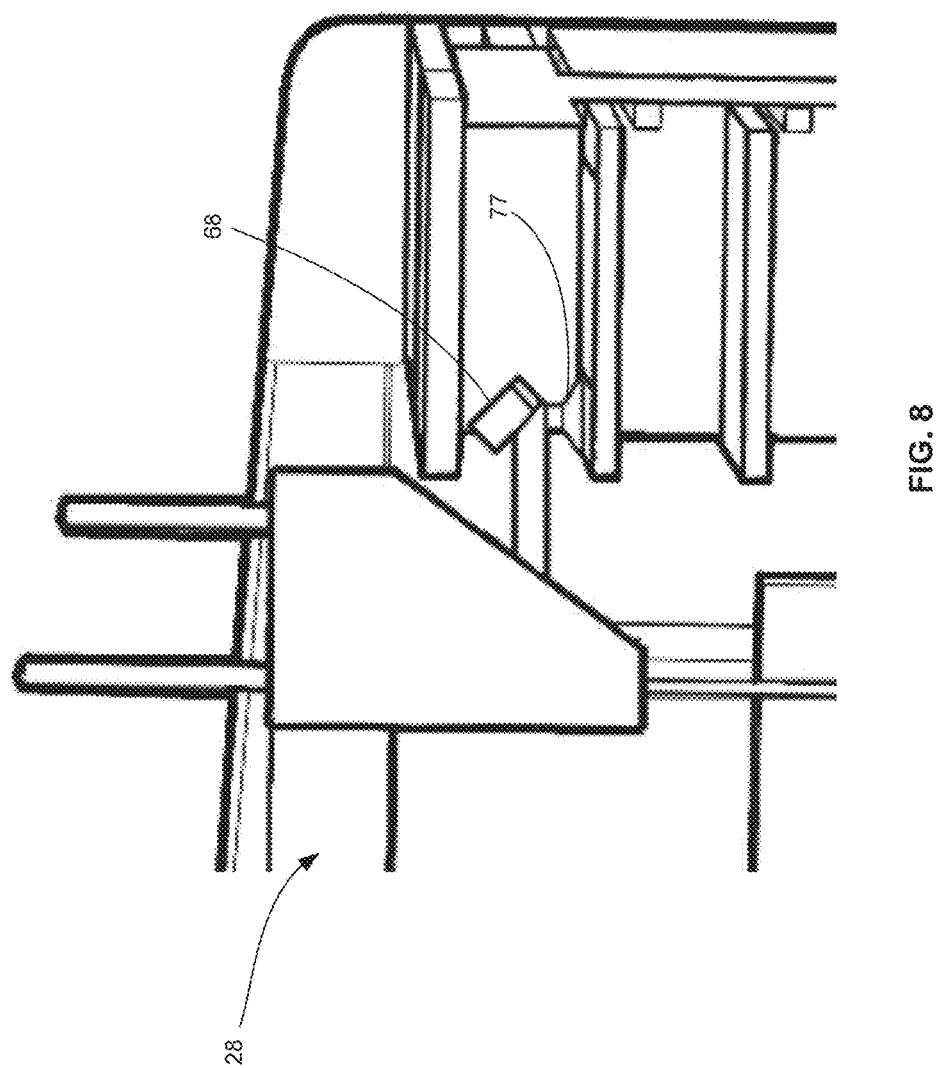
FIG. 8 is a perspective view of input and output buffers, substrate transport device and substrate identifier reader forming part of the apparatus of FIG. 1.

As seen in FIG. 8, a substrate identification reader 68 is supported by, and hence displaced with, the substrate transport device 58. In this embodiment, the substrate transport device 58 comprises a suction device 77 for applying a negative pressure to a particular substrate. The substrate identification reader 68 is disposed so as to read the bar code or other substrate identifier borne by each substrate when the suction device 77 is releasably holding that substrate. It will be appreciated that a variety of other devices could be envisaged for releasably holding and displacing substrates within the apparatus 10.

Figure 9:
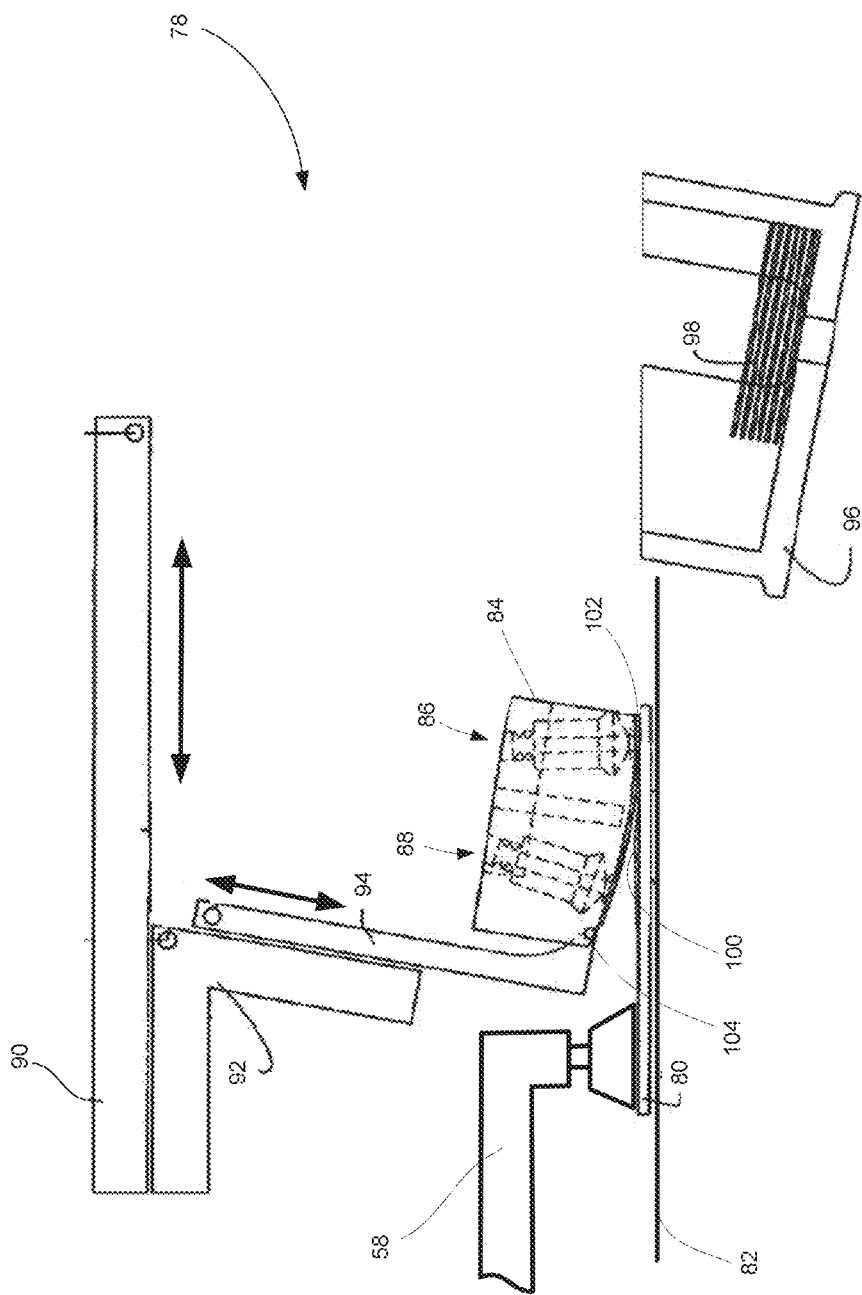
FIG. 9 is cut-away perspective view of a substrate covering unit forming part of the apparatus of FIG. 1.

In various embodiments, the apparatus 10 further includes a substrate covering unit 78, such as a cover slipper, to apply a cover to the biological sample on the substrate. Selected elements of the substrate covering unit 78 is shown in FIG. 9 and more detail is provided in U.S. Pat. No. 6,796,353 in name of Leica Mikrosysteme GmbH, the entire contents of which is hereby incorporated by reference.

The substrate transport device 58 is further configured by the controller 60 to transport individual substrates into and out from the substrate covering unit 78. As can be seen in FIG. 9, the FTP robot 28 and substrate transport device 58 are configured to move each substrate 80 to, and to maintain the substrate 80 in predetermined position on, a horizontal surface 82 in the substrate covering unit 78. A base block 84 including two suction pick up devices 86, 88 is displaced by transport arm 90, linearly movable angle arm 92 and lifting element 94 into a magazine 96 to retrieve a substrate cover (coverslip) 98 by applying a negative pressure from the suction pick up devices 86, 88 to the substrate cover 98. After lifting element 94 has been raised out of magazine 96, it is displaced together with angled arm 92 so that the base block 84 travels into a position above substrate 82. At this time, an adhesive 100 has already been applied onto the substrate 82. The base block 84 is lowered onto the substrate 82. A first end 102 of substrate cover 98 is the first to contact the substrate 82.

A rolling motion of base block 84 results in complete deposition of the substrate cover 98 onto the substrate 82. The base block 84 is joined to lifting element 94 via an articulated joint 104. The base block 84 is pivoted about the articulated joint 104 and in the process rolls along the surface of the substrate 32. During the rolling motion, the negative pressure at the two suction devices 86, 88 is switched off. The base block 84 is then raised, and is ready to pick up a further substrate cover from the magazine 96.

As can be best appreciated from FIG. 2, the treatment stations 12 are disposed on a common work surface 80 in the apparatus 10. In order to optimise the work surface area in the apparatus 10, the reagent containers 26 are housed below the work surface 80, and a reagent transfer system 82 is provided for transferring a reagent from the reagent containers 26 to the reagent dispenser forming part of the FTP robot 28. To that end, the reagent transfer system 82 includes a reagent transfer port 84 passing through the work surface 80. The FTP robot 28 includes a pipette or other aspiration probe for aspiring reagent from the reagent containers 26 via the reagent transfer port 84.

A carousel 86 is provided to support the reagent containers, and to selectively bring each reagent container 26 into fluidic communication with the re-agent transfer port 84. The apparatus 10 may include a reagent container access port 88 (FIG. 1) for loading and unloading the reagent containers to and from the carousel 84. Reagents in the reagent containers may be accessed at the access port 88 via a containers flip lid, piercing tip or like arrangement.

The apparatus 10 may include a heat exchanger (not shown) to cool the reagent containers 26. Advantageously, heat generated by the heat exchanger can then be recirculated to assist in heating steps, such as baking and curing, carried out in the apparatus 10.

It will be appreciate by those persons skilled in the art that the controller 60 can be implemented by a computer remote from the apparatus 10 and connected thereto via a communications network, such as a local area network (LAN) or wireless network. In any case, the controller comprises a number of modules to provide instructions to the BFR 14 and the FTP robot 28 to control movement thereof and the dispensing of re-agents, as well as to control operation of various other devices forming part of the apparatus 10.

Figure 10:
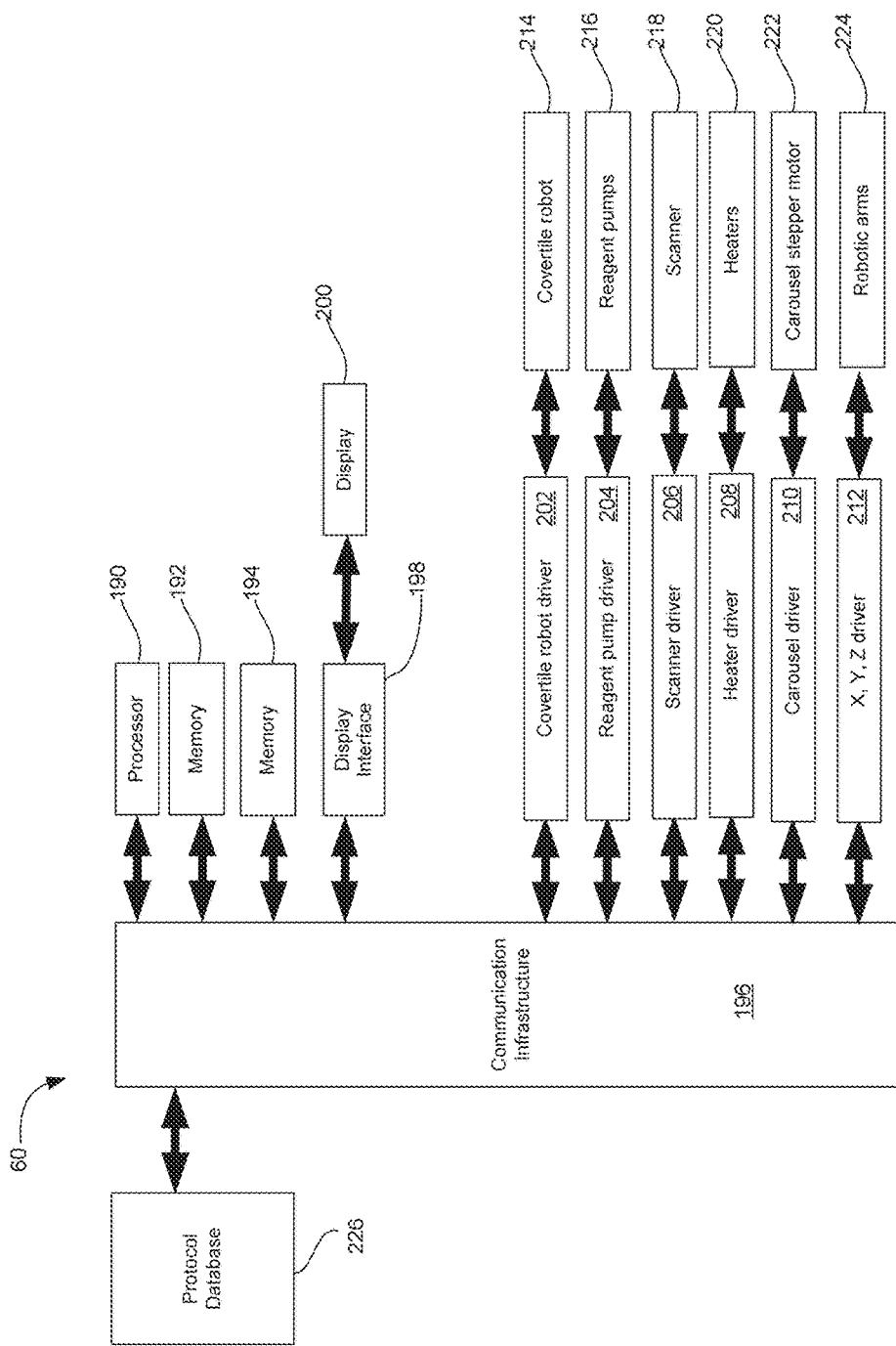
FIG. 10 is a schematic diagram of a controller forming part of the apparatus of FIG. 1.

The controller 60 is shown schematically in FIG. 10, and includes notably a processor 190 in communication with a first memory device 192 for storing computer program code and a second memory device 194 for storing data generated by the processor 190 when implementing the computer program code, via communications infrastructure 196. Moreover, the controller 60 includes a display interface 198 and corresponding display 200 to enable user interaction with the controller 60.

The controller 60 also includes driver modules 202 to 212 for controlling the motors, pumps, scanners, heaters and other devices 214 to 224 required for operation of the apparatus 10. It will be appreciated that in FIG. 10 examples only of driver modules and devices are depicted, and a skilled person in the field will easily be able to determine the driver modules and devices required to implement the apparatus 10 to provide the functionality described herein.

It will be appreciated by persons skilled in the art that the memory devices 192 and 194 may reside in the apparatus 10 or may be hosted remote from the apparatus 10 in data communication with the processor 190. In any event, the processor 190 is configured to read instructions from the memory 192 to operate the apparatus 10 to treat biological samples on substrates. The memory device 192 also includes instructions to identify, displace and treat the substrates from the input buffer 32, to the treatment stations 12 and substrate covering unit 78, to the output buffer 30, in a deterministic way so as to repeatably optimise staining and throughput of the substrates during protocols and/or treatment operations in the apparatus 10. Treatment protocols, including staining protocols (e.g. order of reagents to be dispensed by the BFR 14 and the FTP robot 28 to the substrates) are stored in a protocol database 226 accessible by the processor 190 via the communications infrastructure 196, in order that the processor 190 can configure the BFR 14 and the FTP robot 28 to dispense re-agents to the substrates at the slide treatment stations in the required order and at the appropriate intervals.

The controller 60 may be operably connected to sample tracking systems, such as the Leica® Cerebro™ platform, to allow planning of scheduling, protocol sequencing, reagent requirements, LIS and other connectivity.

Figure 11:
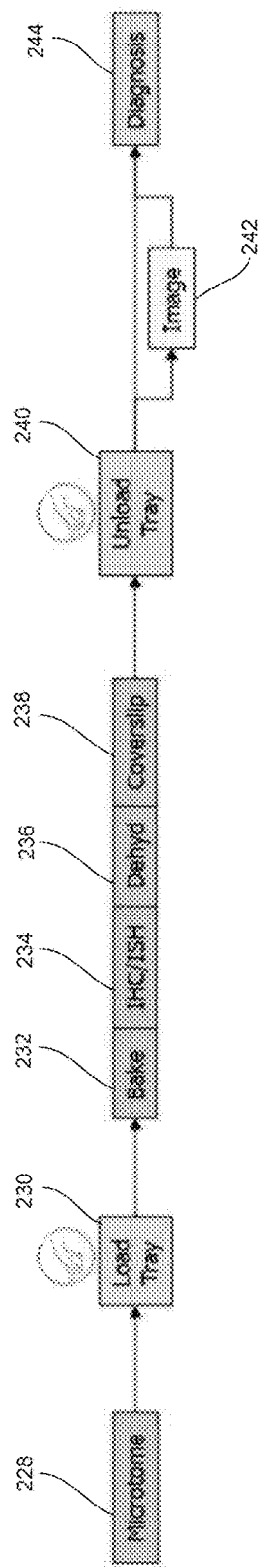
FIG. 11 is a flow chart of a series of operations performed in conjunction with the apparatus of FIG. 1.

As described, the controller 60 is configured to read instructions from the memory 192 to process the substrates in the apparatus 10 according to the protocols and treatment operations defined in the protocol database 226. For example, with reference to the flow chart depicted in FIG. 11, tissue samples may be obtained by sectioning a sample tissue using a microtome at step 228. The tissue samples may then be placed on slides or other substrates by an operator.

These substrates are then loaded into a substrate tray, such as the tray 36 depicted in FIGS. 4 and 5, for placement in a compartment of the input buffer 32 of the apparatus 10, at step 230. The controller 60 then gives instructions to the FTP robot 28 to position the substrate identification reader 68 proximate the substrate identifier borne by each of the substrates. Once the substrate identification reader has read each substrate identifier, the processor 190 determines the protocol to be applied to each substrate in order that individual substrates can be moved to treatment stations 12 within the apparatus 10 in order to optimise throughput of the substrates during protocols and/or treatment operations in the apparatus.

Preferably, the processor 190 selects individual slides and locates these slides at treatment stations so as to group individual substrates to hereby enable the efficient treatment of the biological samples disposed on substrates. Table 1 is an exemplary list of eight substrate trays, each bearing up to five substrates, which are to be treated in the apparatus 10. The eight substrate trays are labelled Tray Nos. 1 to 8.

TABLE 1

| Tray No. | Case No. | Tissue type | Primary Ab |
|---|---|---|---|
| 1 | 1 | Breast | ER, PR, HER2, p63 |
| 2 | 2 | Prostate | p63, CK5, CK14, p504S, PSA |
| 3 | 3 | Melanoma | MelA, S100, HMB45, Ki67 |
| 4 | 4 | Lymphoma | CD3, CD20, CD117, Kappa, Lambda |
| 5 | 4 | Lymphoma | cyclinD1, RET40F, CD68 |
| 6 | 5 | GI | CK7, CK20, CD117, CDX2, DOG1 |
| 7 | 5 | GI | CD34, Ki67 |
| 8 | 6, 7, 8, 9, 10 | Breast | FISH |

Each of the Tray Nos. 1 to 7 supports substrates from a single case (patient). Tray Nos. 1, 2 and 3 each supports substrates from different cases. Tray Nos. 4 and 5 support substrates from same case (Case No. 4), as do Tray Nos. 6 and 7 (which support substrates from Case No. 5). Tray No. 8 supports substrates from multiple cases (Case Nos. 6 to 10).

A series of reagents, including the Primary Antibodies listed in Table 1, is to be applied to the substrates supported by each tray. In order to efficiently treat the biological samples disposed on Tray Nos. 1 to 8, the controller 60 may be configured to cause the substrate transport device 58 to consecutively load individual substrates from the trays to treatment stations in order to group individual substrates to which a common protocol or a common reagent is to be applied. For example, individual substrates from Tray Nos. 1 and 2 both require the application of Primary Antibody p63. Grouping these substrates on the treatment stations 12 reduces the washing steps required to be performed by the FTP robot 28, and maximises the number of substrates to which a common treatment operation is to be applied thereby minimising the number of changes to reagents required to treat all substrates in Tray Nos. 1 to 8.

Other grouping of substrates may also be created in order to efficiently treat the biological samples disposed on Tray Nos. 1 to 8. For example, different treatment operations require the application of reagents, curing, baking or other treatment steps to be carried out for different lengths of time. The substrates in Tray No. 8 to which the FISH antibody is to be applied require a long incubation time, and so may be grouped together for treatment after all other substrates have been treated.

Other substrates may be grouped according to epitope retrieval times whereby a same protocol is applied using different antibodies.

The treatment operations performed in the apparatus 10 may include a baking treatment 232 to dry the tissue sample before staining (by operation of the heating element 74 at a particular treatment station), IHC/ISH operations 234, a dehydration operation 236 where alcohol is applied to the biological sample, and a cover slipper operation 238 performed in the substrate covering unit 78. Once these various operations have been performed, the individual substrates are returned to a vacant slot in a substrate tray in one of the compartments in the output buffer 34.

From here, substrate trays are unloaded at step 240 for subsequent imaging of the substrates at step 242 and diagnosing of the stained tissue samples by a pathologist at step 244.

As has been described above, a number of different processing operations can be performed by the apparatus 10 and notably at the treatment stations in the treatment zone 11, input buffer 32, output buffer 34 and the substrate covering unit 78. These processing operations may include baking, staining, coverslipping, molecular testing (for example polymerase chain reaction), scanning and/or curing of coverslip adhesive. It is to be understood that the apparatus 10 may be used or configured to perform one or a limited number of such processing operations only.

It will be appreciated from the foregoing that movement of individual substrates within the apparatus 10, rather than substrate trays containing multiple substrates, enables grouping of slides having the same protocol or treatment operations. The apparatus 10 can therefore group individual substrates within the treatment zone to efficiently treat the biological samples disposed on substrates. A consequent saving in time and a reduction in the number of probe wash steps required is achieved. The amount of wash fluid consumed by the apparatus 10 is minimised, and a greater increase in the throughput achieved by the apparatus 10 is achieved.

Various other advantages are achieved by the apparatus 10. For example, a smaller footprint of the apparatus 10 is achieved by location of the reagents in a manner to maximise the workspace available for treatment station.

It will be appreciated that the provision of input and output buffers for receiving substrate holders, and the movement and treatment of individual substrates to/from those holders, enables substrates to be loaded into the apparatus 10 in substrate holders by patient case, grouped for efficient treatment within the apparatus 10 and then returned to substrate holders once again by patient case. Such an arrangement minimises or eliminates the sorting and collating of substrates before and after treatment operations that is currently required by known biological sample treatment apparatus.

Moreover, such an arrangement greatly improves laboratory workflow, and reduces handling errors that result from use of known biological sample treatment apparatus.

Further aspects of the method will be apparent from the above description of the apparatus 10. Persons skilled in the art will also appreciate that the method could be embodied in program code. The program code could be supplied in a number of ways, for example on a tangible computer readable medium, such as a disc or a memory or as a data signal or data file (for example, by transmitting it from a server).

It is to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

The invention claimed is:

1. Apparatus for treating biological samples disposed on substrates, including:
    an input buffer for receiving one or more substrate holders each being adapted to support a plurality of the substrates;
    a treatment zone including a plurality of treatment stations each being adapted to receive one of the substrates;
    a reagent dispenser configured by a controller to dispense reagents to the substrates at the treatment stations;
    a substrate transport device configured by the controller to transport individual substrates between the substrate holders in the input buffer and the treatment stations.

2. Apparatus according to claim 1, and further including:
    a substrate identification reader for reading, when the substrate is in the input buffer, a substrate identifier borne by each substrate; and
    a database for storing a plurality of protocols, each protocol defining a sequence of treatment operations to be applied to one or more substrates,
    wherein the controller is further configured to cause the substrate transport device to group individual substrates within the treatment zone to efficiently treat the biological samples disposed on substrates.

3. Apparatus according to claim 2, wherein the controller is configured to perform one or more of:
    a. cause the substrate transport device to group individual substrates to which a common protocol is to be applied;
    b. cause the substrate transport device to group individual substrates to which a common reagent is to be applied;
    c. cause the substrate transport device to group individual substrates that share a common treatment time;
    d. cause the substrate transport device to transport the individual substrates so as to optimise throughput of the substrates during protocols and/or treatment operations in the apparatus; and
    e. maximise the number of protocols or treatment operations that can be consecutively performed on one or more substrates.

4. Apparatus according to claim 3, wherein the controller is configured to optimise the number of reagent dispensing operations performed by the reagent dispenser to different substrates without changing reagents.

5. Apparatus according to claim 2, wherein the substrate identification reader and, optionally the reagent dispenser, is supported by the substrate transport device.

6. Apparatus according to claim 1, and further including:
    a substrate covering unit for applying a cover member to the biological sample on the substrate,
    wherein the substrate transport device is further adapted to transport individual substrates into and out of the substrate covering unit.

7. Apparatus according to claim 1, wherein the treatment stations are disposed on a work surface, and wherein the apparatus further includes:
    a plurality of reagent containers housed below the work surface; and
    a reagent transfer system for transferring reagent from the reagent containers to the reagent dispenser.

8. Apparatus according to claim 7, wherein the reagent transfer system includes:
    a reagent transfer port passing through the work surface; and
    an aspiration probe for aspirating reagent from the reagent containers via the reagent transfer port.

9. Apparatus according to claim 8, wherein the reagent transfer system further includes:
    a carousel supporting the reagent containers, the carousel being adapted to selectively bring each reagent container into fluidic communication with the reagent transfer port, and optionally, further including a reagent container access port for loading and unloading the reagent containers from the carousel.

10. Apparatus according to claim 1, wherein the input buffer includes:
    a plurality of input compartments each adapted to receive one or more of the substrate holders in a disposition whereby the substrates in the substrate holders are accessible to the substrate transport device, and optionally, wherein one or more of the input compartments includes one or more baking stations for baking the substrates in the substrate holders, and further optionally, wherein the compartments are adapted to support the substrate holders in a substantially horizontal orientation.

11. Apparatus according to claim 1, and further including:
    an output buffer for receiving one or more of the substrate holders, wherein the substrate transport device is further configured by the controller to transport individual substrates between the treatment stations and the substrate holders in the output buffer.

12. Apparatus according to claim 11, wherein the output buffer includes:
    a plurality of output compartments each adapted to receive one or more of the substrate holders in a disposition whereby the substrates in the substrate holders are accessible to the substrate transport device and optionally wherein one or more of the output compartments includes one or more curing stations for curing the substrates in the substrate holders.

13. Apparatus according to claim 1, wherein at least one of the substrate holders received in the input buffer supports substrates from a common patient case, and wherein the controller is further configured to group substrates into at least one of the substrate holders received in the output buffer according to that common patient case.

14. An automated method, by the apparatus of claim 1, for treating the biological samples disposed on the substrates, wherein the substrates are treated at the plurality of treatment stations in the treatment zone, the method including the steps of:
receiving the one or more substrate holders in the input buffer, each substrate holder being adapted to support the plurality of the substrates;
using the substrate transport device, configured by the controller, to transport the individual substrates between the substrate holders in the input buffer and the treatment stations;
and using the reagent dispenser, configured by the controller, to dispense the reagents to the substrates at the treatment stations.

15. A method according to claim 14, and further including the step of:
using the substrate transport device, configured by the controller, to transport the individual substrates between the treatment stations and substrate holders in an output buffer for receiving one or more of the substrate holders.

16. A method according to claim 14, and further including the step of:
using the substrate transport device, configured by the controller, to transport the individual substrates into and out of a substrate covering unit for applying a cover member to the biological sample on the substrate.

17. The apparatus according to claim 1, wherein the one or more substrate holders of the input buffer are ones of first substrate holders,
wherein the substrate transport device is further configured by the controller to individually transport one of the substrates from a first slot in one of the first substrate holders in the input buffer to one of the treatment stations,
wherein the substrate transport device is further configured by the controller to individually transport the one of the substrates from the one of the treatment stations to a second slot in one of a plurality of second substrate holders in an output buffer, and
wherein the apparatus comprises the output buffer.

18. The apparatus according to claim 17, wherein the substrate transport device comprises a robotic arm comprising a scanner and a suction cup at an end of the robotic arm.

19. The apparatus according to claim 18, wherein the robotic arm is configured by the controller to
reach into the input buffer, scan, via the scanner attached to an end of the robotic arm, a label attached to the first substrate holder in a first label slot corresponding to the substrate in the first slot,
grip, via the suction cup attached to the end of the robotic arm, the one of the substrates from the first slot of the one of the first substrate holders,
release the one of the substrates into one of the treatment stations,
grip, via the suction cup, the one of the substrates from the one of the treatment stations, and
release the one of the substrates into the second slot in the one of the plurality of the second substrate holders in the output buffer.

* * * * *